(12) United States Patent
Mulier et al.

(10) Patent No.: US 6,585,732 B2
(45) Date of Patent: Jul. 1, 2003

(54) FLUID-ASSISTED ELECTROSURGICAL DEVICE

(75) Inventors: Peter M. J. Mulier, Stillwater, MN (US); Michael F. Hoey, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/955,496

(22) Filed: Sep. 18, 2001

(65) Prior Publication Data

US 2002/0010463 A1 Jan. 24, 2002

Related U.S. Application Data

(63) Continuation of application No. 09/580,228, filed on May 26, 2000, now Pat. No. 6,358,248, which is a continuation of application No. 09/236,034, filed on Jan. 22, 1999, now abandoned, which is a continuation of application No. 08/556,784, filed on Nov. 2, 1995, now Pat. No. 5,897,553, which is a continuation-in-part of application No. 08/393,082, filed on Feb. 22, 1995, now Pat. No. 6,063,081.

(51) Int. Cl.[7] ............................................. A61B 18/14
(52) U.S. Cl. ........................... 606/41; 606/45; 606/46; 606/49; 607/99
(58) Field of Search .......................... 606/41, 42, 45, 606/46, 49; 607/99, 104, 105, 147, 153; 601/17, 20

(56) References Cited

U.S. PATENT DOCUMENTS 3,163,166 A   12/1964   Brent et al.
4,037,590 A   7/1977    Dohring et al.

(List continued on next page.)

FOREIGN PATENT DOCUMENTS

JP   57-117843   7/1982
JP   7-51288     2/1995

(List continued on next page.)

OTHER PUBLICATIONS

Hurst J. Willis, M.D., et al., "Surgicl Treatment of Cardiac Arrhythmias (The Maze Procedure)".
44 Multiple Disease The Heart Arteries and Veins, Seventh Edition, vol. 2, 1990.

*Primary Examiner*—Lee Cohen
(74) *Attorney, Agent, or Firm*—Daniel W. Latham, Esq.; Timothy A. Czaja, Esq.

(57) ABSTRACT

An electrocautery device is disclosed. In accordance with one aspect of the invention, the electrocautery electrode/tip is provided with a hollow, conductive tube terminating at its distal end in a ball point type tip. Fluid, preferably conductive fluid, is applied to the proximal end of the hollow electrode/tip, and expelled from the distal end thereof during electrocautery. The ball point distal tip allows the distal tip to be directly applied to the tissue and "rolled" or slid along the tissue. This allows the distal tip to be moved across the tissue without dragging or snagging on the tissue. In addition, the conductive fluid expelled from the distal tip further lubricates the distal tip as it moves across the tissue. If conductive fluid is used, the conductive fluid emanating from the electrode/tip conducts the RF electrocautery energy away from the distal tip so that it is primarily the fluid, rather than the distal tip that actually accomplishes the cauterizing of tissue. That is, the fluid serves as a "virtual" electrocautery electrode. Since it is the fluid, rather than the distal tip that cauterizes, coagulates and ablates, no burns or perforations are made to the tissue, reducing the amount of debris at the site. Also, the flow of fluid through the electrode/tip tends to keep the distal tip clean and cool.

59 Claims, 2 Drawing Sheets

U.S. PATENT DOCUMENTS

| | | |
|---|---|---|
| 4,307,720 A | 12/1981 | Weber, Jr. |
| 4,920,982 A | 5/1990 | Goldstein |
| 5,242,441 A | 9/1993 | Avitall |
| 5,242,442 A | 9/1993 | Hirshfeld |
| 5,269,781 A | 12/1993 | Hewell III |
| 5,313,943 A | 5/1994 | Houser et al. |
| 5,395,363 A | 3/1995 | Billings |
| 5,431,649 A | 7/1995 | Mulier |
| 5,458,596 A | 10/1995 | Lax et al. |
| 5,487,385 A | 1/1996 | Avitall |
| 5,564,440 A | 10/1996 | Swartz et al. |
| 5,575,810 A | 11/1996 | Swanson et al. |
| 5,640,995 A | 6/1997 | Ockuly et al. |
| 5,643,197 A | 7/1997 | Brucker et al. |
| 5,676,662 A | 10/1997 | Fleischhacker et al. |
| 5,676,693 A | 10/1997 | LaFontaine |
| 5,687,723 A | 11/1997 | Avitall |
| 5,697,927 A | 12/1997 | Imran et al. |
| 5,718,241 A | 2/1998 | Ben-Haim et al. |
| 5,718,701 A | 2/1998 | Shai et al. |
| 5,722,400 A | 3/1998 | Ockuly et al. |
| 5,730,127 A | 3/1998 | Avitall |
| 5,798,960 A | 8/1998 | Stevens et al. |
| 5,800,413 A | 9/1998 | Swartz et al. |
| 5,823,956 A | 10/1998 | Roth et al. |
| 5,855,614 A | 1/1999 | Stevens et al. |
| 5,897,553 A | 4/1999 | Mulier et al. |
| 6,241,754 B1 | 6/2001 | Swanson |
| 6,358,248 B1 * | 3/2002 | Mulier et al. ................ 606/41 |

FOREIGN PATENT DOCUMENTS

| | | |
|---|---|---|
| WO | WO 94/26228 | 11/1994 |
| WO | WO 95/05781 | 3/1995 |
| WO | WO 95/09570 | 4/1995 |
| WO | WO 95/17222 | 6/1995 |
| WO | WO 99/07360 | 3/1996 |

* cited by examiner

FLUID-ASSISTED ELECTROSURGICAL DEVICE

CROSS-REFERENCE TO RELATED APPLICATIONS

This application is a continuation of U.S. patent application Ser. No. 09/580,228, filed May 26, 2000, now U.S. Pat. No. 6,358,248, which is a continuation of U.S. patent application Ser. No. 09/236,034, filed Jan. 22, 1999, now abandoned, which is a continuation of U.S. patent application Ser. No. 08/556,784, filed Nov. 2, 1995 and now U.S. Pat. No. 5,897,553, which is a continuation-in-part of U.S. patent application Ser. No. 08/393,082, filed Feb. 22, 1995, and now U.S. Pat. No. 6,063,081, which applications are incorporated herein by reference.

FIELD OF THE INVENTION

This invention relates generally to the field of medical instruments, and more particularly relates to an electrocautery device.

BACKGROUND OF THE INVENTION

Various types of electrocautery devices for incising and cauterizing body tissue are known and used in the medical field. Typically, such devices include a conductive tip or needle which serves as one electrode in an electrical circuit which is completed via a grounding electrode coupled to the patient. Incision of tissue is accomplished by applying a source of electrical energy (most commonly, a radio-frequency generator) to the tip. Upon application of the tip to the tissue, a voltage gradient is created, thereby inducing current flow and related heat generation at the point of contact. With sufficiently high levels of electrical energy, the heat generated is sufficient to cut the tissue and, advantageously, to simultaneously cauterize severed blood vessels.

It is widely recognized in the prior art that the often substantial amount of smoke produced by electrocauterization of tissue is at least unpleasant, and in some cases distracting or even hazardous to the operator and other attending medical personnel. As a result, it has been proposed, and is common, to provide an electrocautery device with smoke-aspirating capabilities, such that the smoke produced from electrocauterization is quickly withdrawn from the area of incision. Smoke aspiration may be accomplished by providing, in the handle of the electrocautery device near the electrocautery tip/electrode, an inlet port to be coupled to a vacuum or suction source. Examples of this are described in U.S. Pat. No. 4,307,720 to Weber, Jr., entitled "Electrocautery Apparatus and Method and Means for Cleaning the Same;" in U.S. Pat. No. 5,242,442 to Hirschfeld, entitled "Smoke Aspirating Electrosurgical Device;" and in U.S. Pat. No. 5.269,781 to Hewell, entitled "Suction Assisted Electrocautery Unit."

It has also been recognized in the prior art that the accumulation of coagulated blood, tissue rubble, and other debris on the electrode/tip of an electrocautery device can present a problem for the operator, necessitating the periodic cleaning of the tip, e.g., by wiping the tip over sterilized gauze or the like. This is generally regarded as undesirable, since the need to clean the electrode/tip tends to interrupt the incision procedure and increases the risks associated with contamination of the tip or the incision, damage to the tip, injury to the operator, and the like. To address this problem, it has been proposed in the prior art to provide an electrocautery instrument in which the electrode/tip is in slidable engagement with the instrument's handle, such that when the tip is retracted into the hand, any adhering debris automatically scraped off onto the tip of the handle. Such an instrument is proposed in the above-referenced Weber, Jr. '720 patent. While this arrangement may have some benefit, it still may be necessary to wipe off the tip of the handle once the tip is retracted. It is believed that a more direct and effective approach to the problem would be to reduce the amount of debris created during the electrocautery process, thereby eliminating or at least reducing the need to clean the electrode/tip.

Atrial fibrillation is the condition where the normal rhythmic contractions of the heart are replaced by rapid irregular twitchings of the muscular heart wall. At least 1 million people in the U.S. suffer from atrial fibrillation. There are at least three detrimental side effects that occur during atrial fibrillation: a rapid irregular heartbeat; impaired cardiac hemodynamics due to a loss of AV synchrony; and an increased vulnerability to thromboembolism. *Surgical Treatment of Cardiac Arrythmias.* by Willis Hurst pg. 867.

The typical treatment for atrial fibrillation has been to give the patient drugs. For most patients with atrial fibrillation, this therapy has been only moderately effective and has typically produced undesirable side effects.

In view of the problems with drug therapy to treat atrial fibrillation, it has been recognized as desirable to find a surgical treatment that would permanently cure atrial fibrillation. *Cardiovascular Device Update*, July 1995, pg. 1. Although radiofrequency catheter ablation (RFCA) has proven to be a safe and effective way of treating the most benign causes of supraventricular tachycardia (SVT), such as Wolff-Parkinson-White and AV nodal re-entry tachycardia, using ablation to treat atrial fibrillation has proven to be challenging. Id.

The so called "maze" procedure has been developed to treat atrial fibrillation. In the "maze" procedure, incisions are made into the right and left atria via an open chest surgical procedure. These incisions are located to interrupt all the potential re-entry circuit patterns that could occur in the atria and cause atrial fibrillation. The clinical success with the "maze" procedure has been good.

A problem with the "maze" procedure is that it requires open chest surgery which is undesirable. It has been recognized that it would be desirable to duplicate the "maze" procedure with ablation. Id. at pg. 3. This would allow the possibility of performing a "maze"-like procedure thorascopically. However, it has also been recognized that current ablation technology has not developed to allow the "maze" procedure to be duplicated with ablation. Id.

A problem with prior art ablation has been that the ablating tip, if left in contact with a piece of tissue for too long, will burn through and perforate the tissue. In many applications, it has proven difficult to balance leaving an ablating tip in position on a piece of tissue for a sufficient time to allow the tissue to be ablated but not leave it in place for a length of time to burn through and thereby perforate the tissue.

Another problem with prior art ablation devices is that if the ablating tips are left in contact with the tissue too long, the tip "sticks" to the tissue being ablated. In removing the tip, large portions of tissue are often removed attached to the tip. This is not only a result to be avoided because of the tissue damage, but it is time consuming and irritating to the physician. These are clearly problems to be avoided.

SUMMARY OF THE INVENTION

In view of the foregoing considerations, the present invention is directed to an improved electrocautery instrument.

In accordance with one aspect of the invention, the electrocautery electrode/tip is implemented with a hollow, conductive tube terminating at its distal end in a ball point type tip. Conductive fluid is applied to the proximal end of the hollow electrode/tip, and expelled from the distal end thereof during electrocautery. The ball point distal tip allows the distal tip to be directly applied to the tissue and "rolled" or slid along the tissue. This allows the distal tip to be moved across the tissue without dragging or snagging on the tissue. In addition, the conductive fluid expelled from the distal tip farther lubricates the distal tip as it moves across the tissue.

In accordance with another aspect of the invention, the conductive fluid emanating from the electrode/tip conducts the RF electrocautery energy away from the distal tip so that it is primarily the fluid, rather than the distal tip that actually accomplishes the cauterizing of tissue. That is, the fluid serves as a "virtual" electrocautery electrode. Since it is the fluid, rather than the distal tip that cauterizes, coagulates and ablates, no burns or perforations are made to the tissue, reducing the amount of debris at the site of ablation. Also, the flow of fluid through the electrode/tip tends to keep the distal tip clean and cool.

BRIEF DESCRIPTION OF THE DRAWINGS

The foregoing and other aspects of the present invention may perhaps be best appreciated with reference to a detailed description of a specific embodiment of the invention, when read in conjunction with the accompanying drawings, wherein.

DETAILED DESCRIPTION OF A SPECIFIC EMBODIMENT OF THE INVENTION

Figure 1:
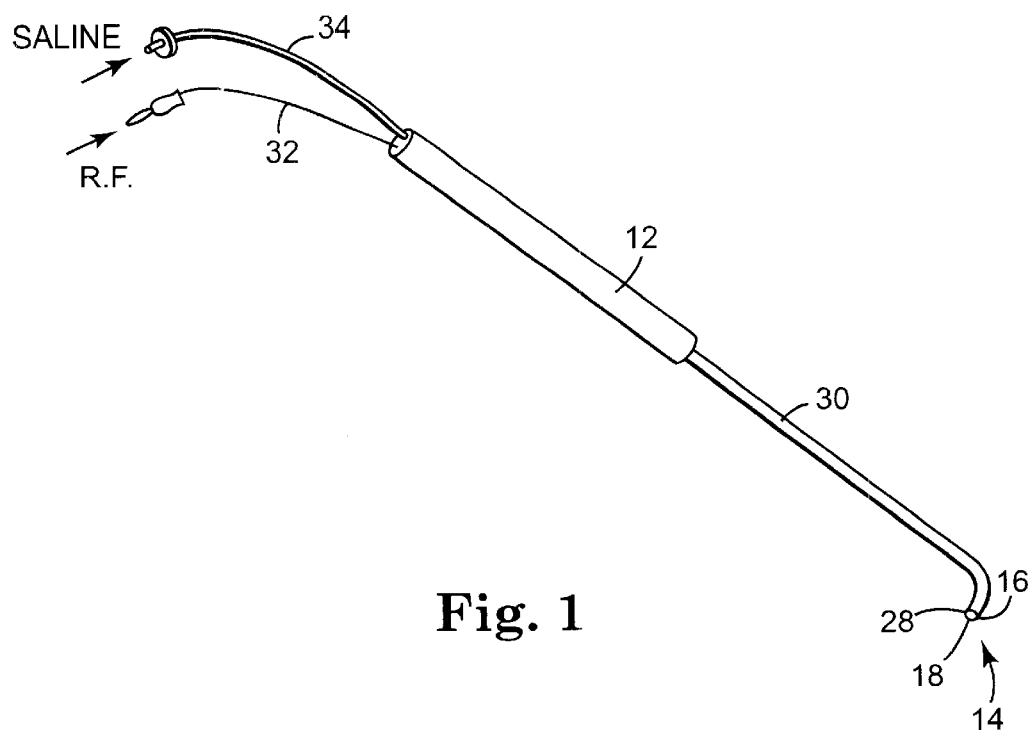
FIG. 1 is a perspective view of an electrocautery instrument in accordance with one embodiment of the invention.

Referring to FIG. 1, there is shown a perspective view of a fluid-assisted electrocautery device 10 in accordance with one embodiment of the invention. Electrocautery device 10 comprises a handle 12 and an electrocautery electrode/tip 14. Handle 12 is preferably made of a sterilizable, rigid, and non-conductive material, such as nylon or the like. Electrode/tip 14 is attached to handle 12.

Figure 3:
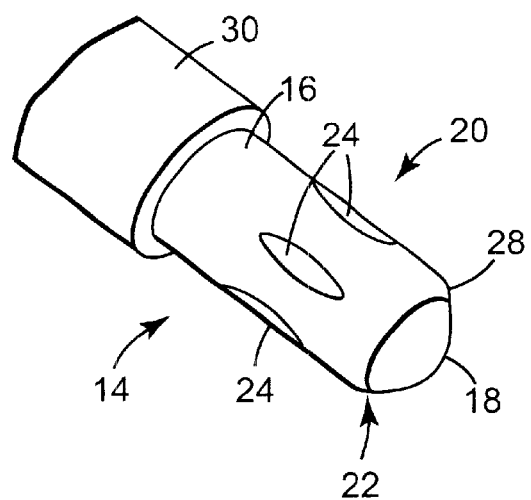
FIG. 3 is a enlarged perspective view of the distal end of the electrocautery device of FIG. 1 showing the electrode/tip.
Figure 4:
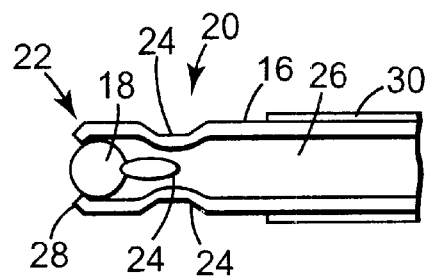
FIG. 4 is a cross-sectional view of the electrode/tip of the device of FIGS. 1, 2 and 3.

In accordance with one aspect of the invention, electrode/tip 14 is preferably implemented using a hollow cylindrical tube 16 with a "ball point" at its distal end, as shown in the greatly enlarged perspective and cross-sectional views of FIGS. 3 and 4, respectively. As can be seen, a ball 18 is retained in a cavity formed by crimping metal tube 16 around ball 18. Both ball 18 and tube 16 are preferably made of an electrically conductive metal such as stainless steel. Tube 16 is crimped both proximal and distal to all 18 at 20 and 22, respectively.

Ball 18 may have any diameter but balls 18 having diameters of from about 1 to about 5 mm have been found to be particularly effective for ablating. Tube 16 must have a diameter corresponding to the diameter of ball 18 as explained herein. Consequently, tube 16 preferably has an internal diameter, particularly at its distal end, of from about 1 to about 5 mm.

Crimping may be accomplished by a number of techniques including but not limited to placing a series of "crimps" 24 around the periphery of tube 16 that are directed toward the interior 26 of tube 16. In addition, the distal end 28 of tube 16 is "crimped" by rounding it toward the interior 26 of tube 16. In this way, ball 18 is retained between the "crimps" 24 and the rounded distal end 28. Crimping should be done so that a portion of ball 18 extends distally beyond distal end 28.

Tube 16 preferably has in interior 26 diameter slightly larger than the diameter of ball 18. In any case, after crimping as described above, the portion of tube 16 surrounding ball 18 should have a slightly larger internal diameter than ball 18. This allows ball 18 to freely rotate between crimps 24 and distal end 28 and still be retained at electrode/tip 14.

An electrical insulator 30 preferably surrounds tube 16 along substantially its entire length, terminating a short distance from distal end 28. Insulator 30 prevents accidental cautery from taking place at locations other than electrode/tip 14 if tube 16 should inadvertently contact patient tissue during a procedure.

Two connections are made to electrocautery device 10. One terminal (e.g., positive) of a radio-frequency (RF) generator (not shown in FIG. 1) is electrically coupled to electrode/tip 14 via a wire 32 attached to tube 16. Contact between ball 18 and tube 16, as will be described in more detail hereafter, provides electrical potential to ball 18.

Figure 2:
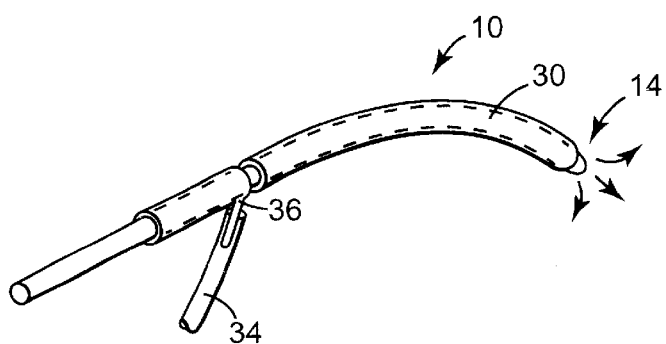
FIG. 2 is a perspective view of the invention separated from the handle.

A source of fluid to be expelled from electrode/tip 14 is coupled to tube 16 via a flexible input line 34. Input line 34 is preferably a tube or hose. Conductive fluid is provided under pressure through tube 16 to the electrode/tip 14. The conductive fluid is introduced to tube 16, as shown in FIG. 2, through input line 34 that is connected to a fluid inlet port 36 on tube 16. Conductive fluid passes from inlet line 34 through fluid inlet port 36 into tube 16 and is communicated along the length of tube 16 to electrode/tip 14 to be expelled from the distal end thereof. This creates a so-called "virtual electrode" for performing electrocautery.

The infusion of conductive fluid simultaneously with the application of RF energy is discussed in further detail in: U.S. patent application Ser. No. 08/113,441 entitled "Method and Apparatus for R-F Ablation," filed on Aug. 27, 1993 in the name of Peter M. J. Mulier and Michael F. Hoey, in U.S. patent application Ser. No. 08/303,246, entitled "Method and Apparatus for RF Ablation," filed on Sep. 8, 1994 in the name of Peter M. J. Mulier; in U.S. patent application Ser. No. 08/302,304 entitled "Method and Apparatus for RF Ablation," filed in the name of Peter M. J. Mulier and Michael F. Hoey on Sep. 8, 1994 and in U.S. patent application Ser. No. 08/393,082 entitled "Fluid Assisted Electrocautery Device", filed in the name of Peter M. J. Mulier and Michael F. Hoey on Feb. 22, 1995. The foregoing '441, '246, '304 and '082 applications (hereinafter collectively referred to as "the RF ablation applications") are each commonly assigned to the assignee of the present invention, and incorporated by reference herein in their respective entireties.

As described in the RF ablation patent applications, the infusion of conductive fluid into the area of application of RF energy creates a "virtual electrode," the size and shape of which can be controllably modified, and which can be rendered more or less conductive, thereby modifying the spread of RF energy. By varying such factors as the RF energy and duration, the rate of infusion of conductive liquid, and the conductivity of the infused solution, the size, shape, and intensity of the "virtual electrode"—i.e., the intensity of thermal production in the area, can be controlled. In the case of the electrocautery device in accordance with the present invention, application of the conductive solution during the application of RF energy further assists by preventing overheating of the electrode/tip, extending the point at which burning or charring of tissue would otherwise normally occur. To enhance this effect, it is contemplated that the solution being infused may first be cooled.

Conductive solutions believed to be suitable for establishing the virtual electrode include saline, saturated saline, and Ringer's solution, among others. Regarding the source of conductive fluid, it is contemplated that a conventional pump may be coupled to input line 34. Alternatively, it is contemplated that a small, pre-pressurized canister of conductive solution may be used, such that no pump is required. In one embodiment, handle 12 may be configured to receive such a pressurized canister therein, eliminating the need for input line 34.

In addition, a dye may be mixed with the conductive fluid to make the fluid more visible during the procedure using the device 10. Examples of such a dye include, but are not limited to methylene blue.

It is desirable to provide the conductive fluid to electrode/tip 14 under pressure that is controlled. In particular, it is important not to have a flow rate that allows conductive fluid to flow excessively out of the distal end 28 of electrode/tip 14. Excessive fluid flow has been shown to spread the electrical current density over a large area of the tissue thereby minimizing, and in some cases preventing, the ablation effect.

In use, electrical potential is applied to tube 16 from a radio-frequency (RF) generator as described above. Since tube 16 is made of an electrically conductive metal, the entire tube 16 will be at an electrical potential determined by the radio-frequency (RF) generator. Conductive fluid is supplied under pressure to the device 10 so that the conductive fluid is expelled from electrode/tip 14 around ball 18.

The user of electrocautery device 10 places electrode/tip 14 at an area to ablate and moves the electrode/tip 14 across the tissue by ball 18 contacting the tissue. Ball 18 may either roll or be slid across the tissue. The fluid expelled from the distal end 28 lubricates the tissue and facilitates the movement of ball 18 across the tissue regardless of whether ball 18 rolls or slides across the tissue.

In vitro experiments have shown the following: The larger the diameter of ball 18, the wider and deeper the ablation "track" created on the tissue; Moving the electrode/tip 14 slowly across the tissue creates deeper lesions than if electrode/tip 14 is moved quickly; and the flow rate of conductive fluid through device 10 and out of electrode/tip 14 should be adequate to wet and lubricate the surface of the tissue but should not be so high as to spread across the tissue and spread the electrical current density necessary to perform the ablation. As examples of desirable flow rates of conductive fluid through the device 10, with a radio-frequency (RF) generator at 50 Watts, a flow rate of about between 0.5 and 2 cc/minute was shown to be adequate and with a radio-frequency (RF) generator at 25 Watts, a flow rate of about between 1 and 2 cc/minute was shown to be adequate. Other flow rates in these power ranges or these or different flow rates for other power settings may also be used as will be clear with practice using the invention. The examples given above being given for the purpose of illustration and are not intended to be limiting.

The device 10 may be particularly used in connection with the so called "maze" procedure described above to ablate an area of the heart to interrupt all the potential re-entry circuit patterns that could occur in the atria and cause atrial fibrillation. The device 10 could also be used advantageously to remove hemorrhoids or varicose veins or stop esophageal bleeding to name but a few possible uses. The device removes the risk of perforation commonly found with other types of cautery, is easy to "write" with and allows deep and wide penetration and subsequently ablation.

Because of its similarity to a ball point pen, the invention provides an electrocautery device 10 that is easy to "write" with. That is, it is easy to move the distal elected/tip 14 across the tissue to be ablated because the ball 18 rolls across the tissue. In addition, by expelling fluid from electrode/tip 14, ball 18 also slides across the tissue being ablated.

Although in the embodiment of FIG. 1, wire 32 and input line 34 are depicted separately, it is contemplated that these connections to device 10 may be consolidated into a single line having a fluid-conducting lumen therein for input of conductive solution alongside an insulated electrical conductor.

Figure 5:
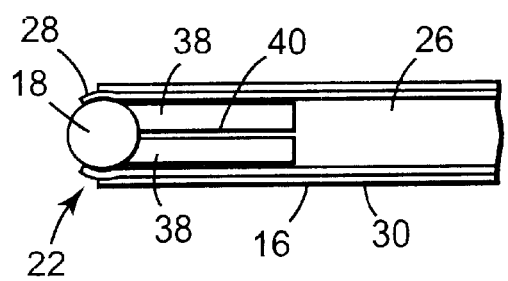
FIG. 5 is a cross-sectional view of another embodiment of electrode/tip of the invention.

Various alternate configurations of electrode/tip 14 are also contemplated. In one embodiment shown in FIG. 5, ball 18 is enclosed within tube 16 at the distal end 28 of tube 16. However, instead of having crimps 24 proximal to ball 18, a block 38 is placed proximal to ball 18 within tube 16. Block 38 preferably has a central lumen 40 exiting from its proximal to its distal end to allow fluid in the interior of tube 16 to pass to ball 18 where it may be expelled from distal end 28. In all other ways, this embodiment is identical to the preferred embodiment described above.

Ball 18 may also be made of a porous, electrically conductive material. In this embodiment, the porous nature of ball 18 allows fluid to not only pass around ball 18 to be expelled from distal end 28, but also allows fluid to pass through ball 18 to be expelled.

In an alternate embodiment, ball 18 may be replaced with a non-spherical contact element such as an electrically conductive elongated plug. In this embodiment, the plug would still be retained in tube 16 at the distal end 28 of tube 16 so that fluid can pass around the plug to expelled from the distal end 28. The plug would be retained by any means described above including, but not limited to, crimps 24 and the rounded distal end 28. However, because the plug is not spherical, the plug can not roll as it is moved in contact across the tissue to be ablated. Instead, the plug will slide across the tissue. In this embodiment, the plug may also be made of an electrically conductive porous material.

Although the invention has been described in connection with using a conductive fluid to create a virtual electrode for electrode/tip 14, it is clear that many of the advantages of the invention such as the smooth flow of electrode/tip 14 will also be produced with the conductive fluid replaced with non-conducting fluid such as pure water. Therefore, it is also within the scope of the invention to include the use of a non-conducting fluid.

In addition, if desired, a suction tube may be added to the device 10 to allow smoke or excess fluid to be removed from the surgical field. Such a suction tube is described in the '082 application described above, the teachings of which have been incorporated by reference herein.

Further, tube 16 may be made of an electrically insulating material except for a portion at its distal end that comes in contact with ball 14. This portion of tube 16 that comes in contact with ball 14 should be electrically conducing. In this embodiment, wire 24 extends to this electrically conducting portion of tube 16.

From the foregoing detailed description of a specific embodiment of the invention, it should be apparent that a method and apparatus for performing fluid-assisted electrocautery of body tissue has been disclosed, wherein fluid delivered out of a hollow electrocautery electrode/tip creates a virtual electrode which incises and cauterizes the tissue.

Although a specific embodiment of the invention has been described herein, this has been done solely for the purposes of illustrating various aspects of the invention, and is not intended to be limiting with respect to the scope of the invention. It is contemplated that various substitutions, alterations, and/or modifications, including but not limited to those specifically discussed herein, may be made to the disclosed embodiment without departing from the spirit and scope of the invention as defined in the appended claims, which follow.

What is claimed is:

1. A method of ablating, through a patient's chest, a length of tissue to replace at least one surgical incision of a Maze procedure for treating atrial fibrillation, the method comprising:
   a. creating an opening in the patient's chest;
   b. inserting a portion of an electrosurgical instrument through the opening in the patient's chest, the electrosurgical instrument comprising:
      (i) an electrode having a proximal end and a distal end, the electrode comprising an electrically conductive tube having an internal lumen extending from the proximal end for delivering a conductive fluid to the distal end, the distal end being rounded and defining at least one opening in fluid communication with the internal lumen,
      (ii) a rigid, non-conductive handle coupled to the proximal end of the electrode,
      (iii) a source of radiofrequency energy electrically connected to the electrode,
      (iv) a source of conductive fluid coupled to the internal lumen of the electrode,
   (c) contacting the tissue to be ablated with the distal end of the electrode;
   (d) delivering conductive fluid from the source of conductive fluid to the electrode such that the conductive fluid is expelled from the distal end of the electrode;
   (e) supplying radiofrequency energy from the source of radiofrequency energy to the electrode; and
   (f) moving the distal end of the electrode along the length of tissue while continuing delivery of conductive fluid and supplying of the radiofrequency energy to create an ablation lesion that replaces at least one surgical incision of a Maze procedure.

2. The method of claim 1, wherein step f includes sliding the distal end of the electrode along the length of tissue.

3. The method of claim 1, wherein step f includes rolling the distal end of the electrode along the length of tissue.

4. The method of claim 1, wherein step f is characterized by moving the distal end of the electrode along the length of tissue without snagging the tissue.

5. The method of claim 1, wherein the conductive fluid lubricates the distal end of the electrode as the distal end of the electrode is moved along the length of tissue.

6. The method of claim 1, wherein as part of step f, the conductive fluid conducts the radiofrequency energy from the distal end of the electrode to the tissue.

7. The method of claim 1, wherein as part of step f, the conductive fluid cleans the distal end of the electrode.

8. The method of claim 1, wherein as part of step f, the conductive fluid cools the distal end of the electrode.

9. The method of claim 8, wherein the conductive fluid is cooled before supplying the conductive fluid to the electrode.

10. The method of claim 1, wherein the conductive fluid is selected from the group consisting of saline, saturated saline and Ringer's solution.

11. The method of claim 1, wherein the source of radiofrequency energy includes a radiofrequency generator.

12. The method of claim 1, wherein the source of conductive fluid includes a pump.

13. The method of claim 1, wherein step d includes supplying between about 0.5 and about 2 cc per minute conductive fluid and step e includes supplying about 50 Watts radiofrequency energy.

14. The method of claim 1, wherein step d includes supplying between about 1 and about 2 cc per minute conductive fluid and step e includes supplying about 25 Watts radiofrequency energy.

15. The method of claim 1, wherein the length of tissue is tissue of the right atria.

16. The method of claim 1, wherein the length of tissue is tissue of the left atria.

17. The method of claim 1, wherein the ablation lesion interrupts potential re-entry circuit patterns that could occur in the atria and cause atrial fibrillation.

18. A method of creating an ablation lesion along a length of tissue of a patient for treating atrial fibrillation, the method comprising:
   a. providing an electrosurgical instrument, the electrosurgical instrument comprising:
      (i) an electrode having a proximal end and a distal end, the electrode defining an internal lumen extending from the proximal end for delivering a conductive fluid to the distal end, the distal end having at least one opening in fluid communication with the internal lumen,
      (ii) a rigid, non-conductive handle coupled to the proximal end of the electrode,
      (iii) a source of radiofrequency energy electrically connected to the electrode,
      (iv) a source of conductive fluid fluidly coupled to the internal lumen of the electrode,
   b. creating an opening in the patient's chest;
   c. inserting the distal end of the electrode through the opening in the patient's chest;
   d. contacting tissue to be ablated with the distal end of the electrode;
   e. delivering conductive fluid from the source of conductive fluid to the internal lumen of the electrode such that the conductive fluid is expelled from the distal end of the electrode;
   f. supplying radiofrequency energy from the source of radiofrequency energy to the electrode; and
   g. moving the distal end of the electrode along a length of the tissue while continuing the delivery of the conductive fluid and the supplying of radiofrequency energy to create an ablation lesion.

19. The method of claim 18, wherein step g is characterized by moving the distal end of the electrode along the length of tissue without snagging the tissue.

20. The method of claim 18, wherein the delivered conductive fluid lubricates the distal end of the electrode as the distal end of the electrode is moved along the length of tissue.

21. The method of claim 18, wherein as part of step g, the delivered conductive fluid conducts the radiofrequency energy from the distal end of the electrode to the tissue.

22. The method of claim 18, wherein as part of step g, the delivered conductive fluid cleans the distal end of the electrode.

23. The method of claim 18, wherein as part of step g, the delivered conductive fluid cools the distal end of the electrode.

24. The method of claim 23, wherein the conductive fluid is cooled before delivering the conductive fluid to the electrode.

25. The method of claim 18, wherein the conductive fluid is selected from the group consisting of saline, saturated saline and Ringer's solution.

26. The method of claim 18, wherein the source of radiofrequency energy includes a radiofrequency generator.

27. The method of claim 18, wherein the source of conductive fluid includes a pump.

28. The method of claim 18, wherein step e includes delivering between about 0.5 and about 2 cc per minute conductive fluid and step f includes supplying about 50 Watts radiofrequency energy.

29. The method of claim 18, wherein step e includes delivering between about 1 and about 2 cc per minute conductive fluid and step f includes supplying about 25 Watts radiofrequency energy.

30. The method of claim 18, wherein the length of tissue is tissue of the right atria.

31. The method of claim 18, wherein the length of tissue is tissue of the left atria.

32. The method of claim 18, wherein the ablation lesion interrupts potential re-entry circuit patterns that could occur in the atria and cause atrial fibrillation.

33. The method of claim 18, wherein the ablation lesion replaces at least one surgical incision of a Maze procedure for treating atrial fibrillation.

34. A method of creating an ablation lesion along a length of tissue of a patient for treating atrial fibrillation, the method comprising:
   a. providing an electrosurgical instrument, the electrosurgical instrument comprising an electrode and a source of radiofrequency energy electrically connected to the electrode;
   b. creating an opening in the patient's chest;
   c. inserting the electrode through the opening in the patient's chest;
   d. contacting tissue to be ablated with the electrode;
   e. supplying radiofrequency energy from the source of radiofrequency energy to the electrode; and
   f. moving the electrode along a length of the tissue without snagging the tissue while continuing the supplying of the radiofrequency energy to create an ablation lesion.

35. The method of claim 34, wherein the source of radiofrequency energy includes a radiofrequency generator.

36. The method of claim 34, wherein step e includes supplying about 50 Watts radiofrequency energy.

37. The method of claim 34, wherein step e includes supplying about 25 Watts radiofrequency energy.

38. The method of claim 34, wherein the length of tissue is tissue of the right atria.

39. The method of claim 34, wherein the length of tissue is tissue of the left atria.

40. The method of claim 34, wherein the ablation lesion interrupts potential re-entry circuit patterns that could occur in the atria and cause atrial fibrillation.

41. The method of claim 34, wherein the ablation lesion replaces at least one surgical incision of a Maze procedure for treating atrial fibrillation.

42. A method of creating an ablation lesion along a length of tissue of a patient for treating atrial fibrillation, the method comprising:
   a. providing an electrosurgical instrument having a proximal end and a distal end, the distal end comprising an electrode and at least one opening in fluid communication with an internal lumen, the internal lumen extending from the proximal end for delivering a conductive fluid to the distal end;
   b. providing a source of radiofrequency energy electrically connected to the electrode;
   c. providing a source of conductive fluid fluidly coupled to the internal lumen;
   d. creating an opening in the patient's chest;
   e. inserting the distal end of the electrosurgical instrument though the opening in the patient's chest;
   f. contacting tissue to be ablated with the distal end of the electrosurgical instrument;
   g. delivering conductive fluid from the source of conductive fluid to the internal lumen of the electrosurgical instrument such that the conductive fluid is expelled from the distal end of the electrosurgical instrument; and
   h. supplying radiofrequency energy from the source of radiofrequency energy to the electrode to create an ablation lesion.

43. The method of claim 42, further comprising moving the distal end of the electrosurgical instrument along a length of the tissue while continuing the delivery of the conductive fluid and the supplying of the radiofrequency energy.

44. The method of claim 43, wherein moving the distal end of the electrosurgical instrument along the length of tissue occurs without snagging the tissue.

45. The method of claim 44, wherein the supplied conductive fluid lubricates the distal end of the electrosurgical instrument as the distal end is moved along the length of tissue.

46. The method of claim 42, wherein the supplied conductive fluid conducts the radiofrequency energy from the electrode to the tissue.

47. The method of claim 42, wherein the supplied conductive fluid cleans at least a portion of the electrode.

48. The method of claim 42, wherein the supplied conductive fluid cools at least a portion of the electrode.

49. The method of claim 42, wherein the supplied conductive fluid is cooled before supplying the conductive fluid to the electrosurgical instrument.

50. The method of claim 42, wherein the conductive fluid is selected from the group consisting a saline, saturated saline, and Ringer's solution.

51. The method of claim 42, wherein the source of radiofrequency energy includes a radiofrequency generator.

52. The method of claim 42, wherein the source of conductive fluid includes a pump.

53. The method of claim 42, wherein step g includes delivering between about 0.5 and about 2 cc per minute conductive fluid and step h includes supplying about 25 Watts radiofrequency energy.

54. The method of claim 42, wherein step g includes delivering between about 1 and about 2 cc per minute conductive fluid and step h includes supplying about 25 Watts radiofrequency energy.

55. The method of claim 42, wherein the length of tissue is tissue of the right atria.

56. The method of claim 42, wherein the length of tissue is tissue of the left atria.

57. The method of claim 42, wherein step h creates an ablation lesion that interrupts potential re-entry circuit patterns that could occur in the atria and cause atrial fibrillation.

58. The method of claim 42, further comprising:

creating an ablation lesion that replaces at least one surgical incision of a Maze procedure for treating atrial fibrillation.

59. A method of ablating, through a patient's chest, a length of tissue in a manner duplicating a pattern of at least one surgical incision of a Maze procedure for treating atrial fibrillation, the method comprising:

a. creating an opening in the patient's chest;

b. inserting a portion of an electrosurgical instrument through the opening in the patient's chest, the electrosurgical instrument comprising:

(i) an electrode having a proximal end and a distal end, the electrode comprising an electrically conductive tube having an internal lumen extending from the proximal end for delivering a conductive fluid to the distal end, the distal end being rounded and defining at least one opening in fluid communication with the internal lumen, (ii) a rigid, non-conductive handle coupled to the proximal end of the electrode, (iii) a source of radiofrequency energy electrically connected to the electrode, (iv) a source of conductive fluid coupled to the internal lumen of the electrode, c. contacting the tissue to be ablated with the distal end of the electrode;

d. delivering conductive fluid from the source of conductive fluid to the electrode such that the conductive fluid is expelled from the distal end of the electrode;

e. supplying radiofrequency energy from the source of radiofrequency energy to the electrode; and f. moving the distal end of the electrode along the length of tissue while continuing the delivery of conductive fluid and supplying of the radiofrequency energy to create an ablation lesion that duplicates a pattern of at least one surgical incision of a Maze procedure.

* * * * *